United States Patent [19]

Huguenard et al.

[11] 4,309,501
[45] Jan. 5, 1982

[54] CRYSTALLIZATION PROCESS

[75] Inventors: Albert P. Huguenard, Le Plessis Trevise; Michel J. Favre, Chantilly, both of France

[73] Assignee: Eastman Kodak Company, Rochester, N.Y.

[21] Appl. No.: 167,163

[22] Filed: Jul. 9, 1980

Related U.S. Application Data

[62] Division of Ser. No. 857,733, Dec. 5, 1977, Pat. No. 4,263,011.

[30] Foreign Application Priority Data

Dec. 9, 1976 [FR] France .................. 76 37070

[51] Int. Cl.³ .............................. G03C 1/02
[52] U.S. Cl. .................... 430/569; 430/568; 430/603
[58] Field of Search ............... 430/569, 567, 568, 603; 23/300, 295 R

[56] References Cited

U.S. PATENT DOCUMENTS

| | | | |
|---|---|---|---|
| 2,757,126 | 7/1956 | Cahn | 23/300 |
| 3,190,748 | 6/1965 | Landgraf | 75/108 |
| 3,375,082 | 3/1968 | Graf | 23/295 |
| 3,392,539 | 7/1968 | Grimmett | 62/58 |
| 3,394,995 | 7/1968 | Kloepfer et al. | 159/45 |
| 3,415,650 | 12/1968 | Frame et al. | 430/569 |
| 3,461,679 | 8/1969 | Goldberg | 23/300 |
| 3,668,142 | 6/1972 | Luckey | 252/301.5 |
| 3,785,777 | 1/1974 | Porter et al. | 23/271 |
| 3,801,326 | 4/1974 | Claes | 430/567 |
| 3,897,935 | 8/1975 | Forster et al. | 259/4 |
| 4,022,820 | 5/1977 | Johnson | 422/245 |
| 4,159,194 | 6/1979 | Steward | 422/245 |

FOREIGN PATENT DOCUMENTS

| | | |
|---|---|---|
| 2116124 | 7/1972 | France . |
| 597068 | 1/1948 | United Kingdom . |
| 1005823 | 9/1965 | United Kingdom . |
| 1365536 | 9/1974 | United Kingdom . |

*Primary Examiner*—Travis Brown
*Attorney, Agent, or Firm*—A. P. Lorenzo

[57] ABSTRACT

Fine crystals characterized by improved morphological homogeneity and a narrow size distribution are prepared by introducing a solution of a crystallizable solute in a solvent into a bed of small inert continuously moving solid particles and initiating crystallization within the solution while it is in contact with the moving particles. The process finds application in the manufacture of diverse crystalline products such as, for example, in the formation of metal oxalates, phosphorescent compounds, and silver halide crystals, as well as in the purification of both organic and inorganic materials.

11 Claims, 10 Drawing Figures

CRYSTALLIZATION PROCESS

This is a division, of application Ser. No. 857,733, filed Dec. 5, 1977, now U.S. Pat. No. 4,263,011.

BACKGROUND OF THE INVENTION

1. Field of the Invention

This invention relates in general to the art of crystallization and in particular to a novel process for the preparation of fine crystals. More specifically, this invention relates to a crystallization process specifically adapted to the preparation of fine crystals which are characterized by improved morphological homogeneity and a narrow size distribution.

2. Description of the Prior Art

Processes of crystallization are extensively utilized in many different branches of industry. In some instances, the processes are characterized by the chemical reaction of two or more compounds to form a reaction product which precipitates from the reaction medium in crystalline form. In other instances the processes are purification procedures in which a solid product to be purified is dissolved in a liquid which is a better solvent for the impurities to be removed than for the product itself and the product is precipitated in crystalline form while the impurities remain in solution. In purification processes, various means can be utilized to initiate the crystallization, for example, alteration of the temperature or addition of a second liquid to the system in order to change the solubility limit and thereby cause precipitation to take place. Both in the instance of a chemical reaction forming a crystalline product and the use of crystallization as a purification technique, the characteristics of the resulting crystals are significantly influenced by such factors as the operating conditions of the process and the type of equipment used in carrying out the process.

Among the important properties of a crystalline product are the morphology of the crystals, their dimensions, and their size distribution. In some intances it is highly desirable that a crystalline product be produced in a very finely divided state, i.e., in the form of fine crystals such as crystals having a particle size of about one micron or less. Examples of products in which this can be an important criterion are metal oxalates which are to be used in the production of magnetic particles intended for use in magnetic recording, phosphorescent compounds which are used, for example, in the preparation of X-ray intensifying screens, and silver halides used in the manufacture of radiation-sensitive photographic materials. Many other examples of products in which a fine crystalline form is advantageous can also be mentioned, such as pigments for use in paints, catalysts used in heterogeneous catalysis, and pharmaceutical products whose physiological effectiveness is influenced by their surface area. In addition to producing crystals of fine size, it is often important to be able to produce crystals which are morphologically homogeneous, i.e., which do not differ significantly from one to another in crystalline form, and which are all of substantially the same size, i.e., within a narrow size distribution.

The prior art has encountered difficulty in producing fine crystals characterized by morphological homogeneity and a narrow size distribution, particularly in a continuous or flow through preparation mode. Thus, for example, differences in temperature or in concentration at different points within the vessel in which crystallization is carried out, especially when the vessel is of large size, contribute toward the formation of a crystalline product with a broad size distribution. In many crystallization processes there is a tendency for a crust to form on the walls of the vessel, especially when the walls are subjected to cooling, and this crust can be composed of interlaced crystals forming a separate population from the main body of crystals, i.e., displaying different morphological characteristics. Back-mixing within the reaction vessel can lead to very disparate crystal sizes. Also, random nucleation due to poor control of the conditions at the beginning of the crystallization can lead to crystals of disparate morphology and dimensions. Reproducibility of the process may be especially unsatisfactory. Attempts to avoid these problems have been the subject of extensive effort in the past by persons working in the field of crystallization processes. Many different approaches seeking to solve one or more of the aforesaid problems have been described in the patent literature, for example, in U.S. Pat. No. 3,190,748-pertaining to the manufacture of metal oxalates, in British Pat. No. 1,365,536 pertaining to the use of crystallization columns in purification and/or concentration processes, in U.S. Pat. No. 3,668,142 pertaining to the preparation of phosphors, and in U.S. Pat. Nos. 3,801,326 and 3,897,935 pertaining to the manufacture of silver halide crystals.

It is toward the objective of providing a simple, practical and highly efficient process for preparation of fine crystals characterized by morphological homogeneity and a narrow size distribution that the present invention is directed.

SUMMARY OF THE INVENTION

In accordance with the present invention, it has been discovered that fine crystals characterized by improved morphology and a narrow size distribution can be prepared by a process comprising the steps of (1) providing a solution of a crystallizable solute in a solvent, (2) bringing the solution into contact with a bed of small, inert, continuously moving solid particles, (3) initiating crystallization within the solution while it is in contact with the moving particles to precipitate the solute in crystalline form, and (4) recovering the precipitated crystals. The method can be used in any situation where it is desired to obtain fine crystals with the aforesaid characteristics. For example, it can be used in processes wherein two or more chemicals react with one another to form a crystalline product or in recrystallization processes utilized to purify crystalline materials of either organic or inorganic types. It finds particular advantage when utilized in, for example, the preparation of metal oxalates, phosphorescent compounds, and silver halides.

DESCRIPTION OF THE PREFERRED EMBODIMENTS

Figure 1:
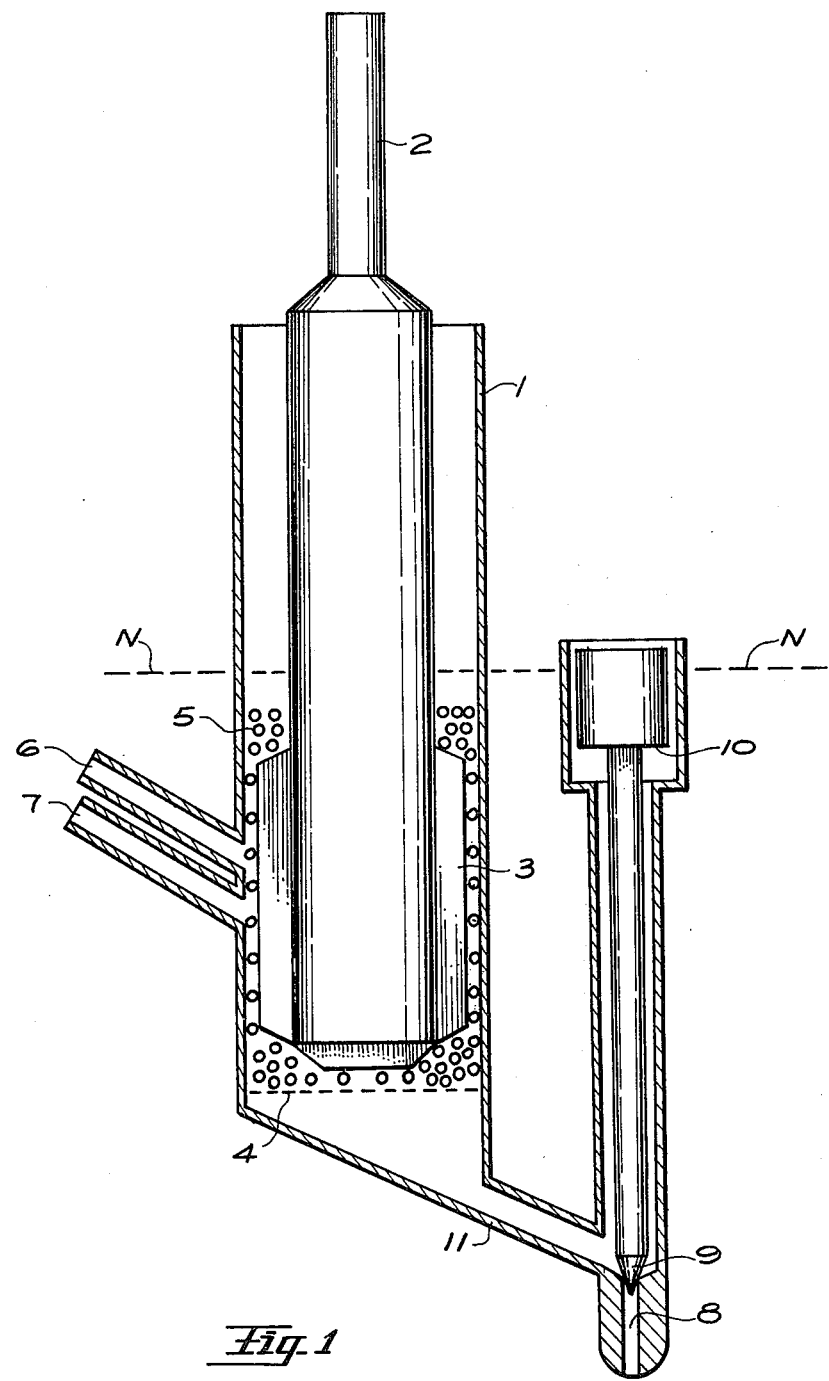
FIG. 1 is a sectional view of an apparatus adapted to continuous preparation of high-density crystalline powders by the method of this invention.

Crystalline materials that can be prepared by the method of this invention include organic and inorganic compounds of any type which are advantageously produced in the form of small-size crystals, e.g. crystals which are typically about one micron or less in size, displaying good morphological homogeneity and a narrow size distribution. The crystallizable material can be a single compound or a mixture of two or more compounds so that the term "solute" as employed herein is intended to encompass mixtures as well as individual compounds. Similarly, the liquid medium from which crystallization takes place can be a single liquid or a mixture of two or more liquids so that the term "solvent" as used herein is intended to encompass a medium made up of one or more liquids in which the solute is dissolved. The process of crystallization can be carried out in a batch, semi-continuous or continuous manner as desired. As indicated hereinabove, it is useful in crystallization processes involving chemical reaction to form a crystalline precipitate, such processes being referred to herein as reaction-crystallization processes, and in crystallization processes whose object is separation of crystals in pure form from impurities with which they are associated, such processes being referred to herein as purification-crystallization processes. The method is applicable both to crystallization processes that occur substantially instantaneously and to those which require an incubation time and is especially advantageous in regard to the latter type of process in that it tends to minimize the incubation period required. Crystallization can be initiated in the process of this invention by exerting a physical or chemical action on the solution of crystallizable solute, as hereinafter described in greater detail. An essential characteristic of the process is that the crystallization be initiated while the solution is in contact with small, inert, continuously moving solid particles, for example, with the solution in contact with a bed of continuously agitated glass beads.

In carrying out reaction-crystallization processes by the method of this invention, a first solution containing a first reactive solute is combined with a second solution containing a second reactive solute, with the two solutions being brought into contact in the midst of a bed of small, inert, continuously moving solid particles such as glass beads. The term "reactive" as used herein in regard to the solutes is intended to mean capable of reacting chemically with one another. Thus, the first solute reacts chemically with the second solute to form an insoluble crystalline product which precipitates from the reaction medium. In carrying out purification-crystallization processes by the method of this invention, the substances to be purified is dissolved in a suitable solvent and while the solution is in contact with the bed of moving particles it is subjected to appropriate treatment, such as a lowering of the temperature, that brings it to a state of oversaturation with respect to the product to be recovered. As a result, the product precipitates in a substantially pure crystalline state and the impurities remain in solution. This technique can also be used to separate the constituent of a mixture, for example to separate isomers by causing the less soluble isomer to crystallize.

While applicants do not know with certainty the mechanism whereby their invention achieves the advantageous results obtained and do not wish to be bound by any theoretical explanation, it is believed that the method of this invention achieves the desired result of production of fine crystals characterized by improved morphology and a narrow size distribution through a number of interrelated effects. Thus, for example, the mechanical action of the continuously moving solid particles is very effective in imparting uniform and intense agitation to the solution from which the crystals are precipitated. Moreover, contact of the moving particles with the walls of the reaction vessel effectively avoids the formation of a crust on the wall surface and thereby avoids the possibility that crust formation will contribute to undesirable morphological heterogeneity. The use of moving solid particles is also advantageous in that each element of volume defined within the bed of moving particles constitutes a cell wherein the reaction conditions are perfectly defined and this contributes to the formation of a homogeneous crystalline product. In addition, the frictional contact between the moving solid particles and the walls of the reaction vessel can result in the generation of minute particles, hereinafter referred to as microparticles, which are broken away from the walls and/or the moving solid particles that make up the bed. These microparticles, for example, microparticles composed of glass, can be very effective in inducing nucleation with certain types of crystalline products, for example, metal oxalates. Since they represent freshly created surfaces they are particularly active in this regard and since they are formed in large numbers the result is the formation of numerous nuclei, whereby the desired objective of forming crystals of very small size is promoted. The fluid dynamics in a reactor comprising a bed of continuously moving solid particles, as described herein, are also such as to favor the formation of a crystalline product with the desired characteristics of small size, morphological homogeneity and narrow size distribution. For example, in using the reactor in a continuous precipitation process it is characterized by a form of "plug flow" in which there is a high degree of mixing in the radial direction but limited back-mixing.

In the process of this invention, crystallization can occur spontaneously in the reaction vessel upon bringing the reactants together or can be initiated by either physical or chemical action. For example, the crystallization can be initiated by modifying the temperature of the solution, usually by cooling it. The change in temperature brings the solution to a point of over saturation with the result that a crystalline precipitate is formed. Several different materials dissolved in the solution can crystallize in the form of a combination, for example, in the formation of double salts such as alums. An alternative technique to initiate crystallization is evaporation of the solvent, either under atmospheric pressure or vacuum, to bring the solution to a point of oversaturation and thereby cause precipitation. The initiation of crystallization can, as previously indicated, be brought about by the introduction of an agent which reacts chemically with the solute to yield a crystalline precipitate. Modification of the solvent composition by addition of a liquid which is miscible with the solvent but is itself a non-solvent or poor solvent for the solute is also an effective method of initiating crystallization.

In the process of this invention, small inert continuously moving solid particles are maintained in contact with the solution which is treated in a suitable manner, as described above, to initiate crystallization. The term "inert" as used herein in referring to these particles is intended to indicate that they do not react with the solute, or otherwise interfere in the desired formation of crystals, and do not dissolve in the solution from which the crystals are precipitated. In a preferred embodiment of the invention the solid particles are spherical in shape and in a particularly preferred embodiment they are glass beads. Particles of a shape other than spherical and particles of a material other than glass can, of course, also be used with satisfactory results. For example, the particles can be metallic beads such as beads composed of stainless steel, or beads formed from an organic polymeric material. The optimum dimension of the moving particles will depend upon a variety of factors, such as the volume of the reaction vessel and the desired dimension of the crystalline product. Generally speaking, the optimum dimension will increase with increasing reactor volume. It may be advantageous in certain instances to use a mixture of particles of different diameters. The optimum material for the particles is dependent upon the product being produced. Glass beads have proven to be very well adapted to use in a variety of situations but in some cases it may be desirable to use other materials such as metal beads. Mixtures of different kinds of particles, particularly mixtures of beads of different hardness can be advantageously employed. This is especially the case in view of the fact that abrasion products of the beads are capable in certain instances of playing a role in nucleation, as described hereinabove, and the degree to which abrasion products are formed will be affected by hardness.

As a typical example, with a reactor having an effective volume of 100 milliliters an optimum size for the beads is a diameter in the range from about 0.1 mm to about 3 mm. In other situations, smaller beads, or larger beads such as those having a diameter of up to 10 millimeters or more can be utilized.

In continuous reaction-crystallization processes, crystal size is, of course, affected by many factors including the flow rate of the reactants, with increased flow rate tending to result in a decrease in the average size of the crystals, and the concentration of the reactants, with decreased concentration tending to result in a decrease in the average size of the crystals. Additional factors affecting crystal size include the temperature at which the reaction takes place, the size and geometry of the reactor, the size and geometry of the moving solid particles, and the degree of agitation to which the solid particles are subjected.

The bed of solid particles utilized in the process of this invention can be agitated to keep the particles in continuous motion by any suitable means. For example, agitation can be provided by mechanical vibration, by pulsations induced by a pump, by the use of ultrasonics, by rotating impellers, by rotating stirring devices equipped with flexible or rigid blades, by Archimedean-screw stirrers, and so forth. In using rotating stirring devices, these will typically be rotated at a speed in the range from about 50 revolutions per minute to about 2000 revolutions per minute. The agitation should be such as to ensure homogeneous conditions concerning temperature and concentration at all points in the medium wherein crystallization occurs.

The method of this invention can be effectively carried out by the introduction of successive charges to the crystallization apparatus but is particularly advantageous, due to the short incubation period that characterizes the process, for continuous preparation. The process provides all the advantages inherent to continuous operation such as flexibility, high yield and avoidance of the need for bulky equipment, while at the same time achieving the desired results in regard to the characteristics of the crystals, that is, providing crystals which are of small size, have a narrow size distribution, and are of improved morphological homogeneity and are typically morphologically homogeneous.

In a typical example of the process of this invention, iron/cobalt oxalate crystals are produced by mixing and reacting within a bed of continuously agitated glass beads an oxalic acid solution and a solution containing ferrous chloride and cobalt chloride.

It is known that simple or mixed oxalates of elements, such as iron, cobalt, nickel, zinc and manganese provide, through decomposition on heating, either the corresponding oxide or mixture of oxides when the decomposition occurs in an oxidizing atmosphere, or the corresponding metal or metal alloy when it occurs in a reducing atmosphere. The state of division of the pyrolysis products is, of course, dependent upon the crystalline characteristics of the oxalates which are decomposed. The pyrolysis products can be used in catalysis, in the preparation of ferrites, or in the manufacture of certain types of magnets. Metallic powders are also very useful in the manufacture of magnetic recording elements, such as magnetic tape, particularly when high data density recording materials are desired. Numerous technical articles describing such materials have been published, for example, see the article entitled "A Critical Review of Magnetic Recording Materials", Geoffrey Bate and J. K. Alsted, IEEE Transactions on Magnetics, Vol. MAG 5, No. 4, December 1969. To achieve the desired performance, the metallic powders must be in the form of particles, preferably aciculae, having a length of one micron or less, a very narrow size distribution, and morphological homogeneity. The method of this invention is well suited to the preparation of the aforesaid simple or mixed oxalates having characteristics that render them suitable for preparation of such metallic powders. The oxalates are typically prepared by reaction of oxalic acid with a metal chloride or mixtures of metal chlorides.

In a further typical example of the process of this invention, calcium tungstate, a common example of a phosphor, is manufactured by the reaction, within a continuously agitated bed of glass beads, of potassium tungstate dihydrate ($K_2WO_4 \cdot 2 H_2O$) and calcium chloride ($CaCl_2$). The process of this invention is equally useful in the manufacture of many other phosphors such as, for example, barium lead sulfate, zinc cadmium sulfide, lead-activated barium silicate, lead-activated strontium sulfate, gadolinium-activated yttrium oxide, europium-activated barium strontium sulfate, europium-activated barium lead sulfate, europium-activated yttrium vanadate, europium-activated yttrium oxide, europium-activated barium phosphate, terbium-activated gadolinium oxysulfide, terbium-activated lanthanum oxysulfide, magnesium gallate, and the like. These phosphors have many important uses such as in the manufacture of screens for color television tubes and in the manufacture of intensifying screens for radiographs. Often, such crystal properties as size, morphology and size distribution are critical factors with respect to the utility of such materials.

The process of this invention is also highly advantageous for use in the manufacture of radiation-sensitive silver halide emulsions. The specialized nature of the photographic emulsion art has led to the historical development of an argot generally understood and employed by those skilled in the manufacture of silver halide emulsions. Emulsions having a relatively high uniformity of grain size are referred to in the art as "monodispersed" emulsions. A quantitative definition which illustrates monodispersed emulsions is contained in Illingsworth U.S. Pat. No. 3,501,305. Those emulsions which are not monodispersed are said to be "polydispersed" or "heterodispersed". The silver halide emulsions prepared by the present process are not monodispersed, but they can be significantly less polydispersed than comparable emulsions prepared by continuous silver halide precipitation techniques where back-mixing of reactants occurs in the reaction vessel. All of the radiation-sensitive silver halide crystals prepared by the present process can be fairly characterized as being fine grains in a generally accepted sense of the term. However, since photographic emulsions almost exclusively employ silver halide grains of less than 2 microns in diameter, typically less than 1 micron, in the specialized terminology of that art, the silver halide emulsions which can be prepared by the practice of this process include intermediate and fine grain emulsions. This process is particularly suited to preparing silver halide emulsions having an average grain size of less than about 0.4 micron.

The batch preparation of radiation-sensitive silver halide emulsions is old and well known in the art. To form a radiation-sensitive silver halide emulsion a silver salt is reacted with at least one halide salt in the presence of a peptizer. In one approach, referred to in the art as a single-jet precipitation technique, one reactant (usually the halide salt) and at least a portion of the peptizer are loaded into a reaction chamber and the other salt (usually the silver salt) is introduced in a single jet. In an alternative approach, referred to in the art as a double-jet precipitation technique, the silver and the halide salts are introduced concurrently into the reaction chamber in separate jets. Such parameters as desired crystal habit and size-frequency distribution of the silver halide grains affect the specific silver halide precipitation techniques to be employed.

Although radiation-sensitive silver halide emulsions are most commonly prepared by either single-jet or double-jet batch precipitation processes, it is known that radiation-sensitive silver halide emulsions can be prepared by continuous silver halide precipitation techniques. A continuous silver halide emulsion forming technique can be viewed as a modified form of a double-jet batch precipitation technique wherein a portion of the silver halide emulsion is removed while silver halide grain formation is still occurring. Typically a continuous precipitation technique is performed under steady-state conditions wherein the rate of removal of silver halide grains and peptizer from a reaction chamber balances the rates of reactant and peptizer additions. The emulsion withdrawn from the reaction chamber is a polydispersed emulsion, since the silver halide grains differ as to their individual residence times within the reaction chamber. However, an invariant output in terms of average grain size, crystal habit and size-frequency distribution is obtainable under steady state operating conditions. Illustrations of conventional continuous silver halide emulsion forming techniques are provided by Halwig U.S. Pat. No. 3,519,425, issued July 7, 1970, and Zelikman and Levi, *Making and Coating Photographic Emulsions,* Focal Press, pp. 228-234. It is to be particularly noted that Zelikman and Levi at page 228, FIG. 122, suggest two stage, or cascade, continuous silver halide emulsion formation. (A discussion of cascade crystallization not related to silver halide compositions is given by M. A. Larson and P. R. Wolff, *Crystal Size Distribution from Multistage Crystallizers,* Chemical Engineering Progress Symposium Series, 67, No. 110, 97-107, 1971).

In utilizing the process of this invention for the continuous manufacture of radiation-sensitive silver halide emulsions, the silver salt and the halide salt or salts are separately introduced into the reaction chamber. The reaction medium is typically an aqueous medium, and water soluble silver salts, such as silver nitrate, and water soluble halide salts, such as alkali halide salts, most commonly sodium or potassium halide salts, are introduced into the reaction chamber. In an aqueous medium the peptizer is typically a hydrophilic colloid, such as gelatin, which can be introduced with either or both of the silver and halide salts or separately therefrom. It is recognized that the silver and the halide salts can include any conventional counter ion which allows for desired solubility in the reaction medium and which is not incompatible with the silver halide grain-forming reaction. A wide variety of both aqueous and nonaqueous silver halide grain-forming double-jet reaction techniques and reactants for use therein are taught in the art. A thorough discussion of conventional silver halide precipitation reactions can be found in the following references: *Photographic Chemistry,* Pierre Glafkides, Fountain Press, London, 1958, pp. 327-330; *Nucleation in Silver Bromide Precipitation,* C. R. Berry and D. C. Skillman, J. Phys. Chem., 68, 1138-43 (1946); C. R. Berry and D. C. Skillman, J. Photo Sci., 68, 121-133 (1964); and *The Theory of the Photographic Process,* Third Edition, C. E. K. Mees and T. H. James, Macmillan, 1966, Chapter 2; Berry, *Rate Processes in AgBr Crystal Growth,* Photog. Sci. and Engr., 18, 4-8, (1974); Berry, *A New Model for Double-Jet Precipitations,* Photog. Sci. and Engr., 20, 1-4, (1976).

The process of this invention is useful for the preparation of all of the various types of silver halides such as, for example, silver bromide, silver chloride, silver bromoiodide, silver chlorobromide, silver chloroiodide, and silver chlorobromoiodide. The silver halide crystals with improved morphological homogeneity and relatively reduced heterodispersity as compared to back-mixing continuous precipitation processes that are produced by the process of this invention are especially useful in higher contrast photographic emulsions.

In adapting the process of this invention to use in the continuous preparation of radiation-sensitive silver halide emulsions, considerable variation in process parameters is usually feasible. For example, the precipitation can be carried out at temperatures in the range from about 25° C. to about 80° C. Generally speaking, increased crystal size will result from increases in temperature. Residence time in the reactor can also vary widely, with residence times in the range of from about 10 seconds to about 10 minutes being typically employed and most frequently in the range from about 20 seconds to about 5 minutes. Very short residence times promote the formation of very small crystals and, correspondingly, an increase in residence times tends to result in an increase in crystal size. Residence time is the average time it takes liquid to flow from an inlet to an outlet through the reaction chamber.

The process of this invention can be readily adapted to the manufacture of ammoniacal silver halide emulsions as taught for example by Gutoff U.S. Pat. No. 3,773,516, issued Nov. 20, 1973, or to the manufacture of silver halide emulsions in which the silver halide grains are formed in the presence of a sulfur-containing silver halide ripening agent, as taught by Terwilliger et al, U.S. Pat. No. 4,046,576. The ripening agent can be introduced into the reaction chamber along with any one or combination of the other materials, or entirely separately if desired.

Useful sulfur-containing silver halide ripening agents include thioether ripening agents such as those disclosed in McBride U.S. Pat. No. 3,271,157, issued Sept. 6, 1966, the disclosure of which is incorporated herein by reference. The thioether is typically introduced at a rate sufficient to produce a concentration of from 0.05 to 50 grams per mole of silver halide in the emulsion being withdrawn from the reaction chamber, with about 0.1 to 20 grams of thioether per mole of silver halide being preferred.

Certain of the preferred organic thioether silver halide solvents can be represented by the formulas:

$$Q-[(CH_2)_r-CH_2-S-(CH_2)_2-X-(R)_p-(CH_2)_2-(R')_q-S-CH_2-(CH_2)_m-Z]_n$$

and $$Q-(CH_2)_m-CH_2-S-(CH_2)_n-S-CH_2-(CH_2)_r-Z$$

wherein:
r and m are integers of 0 to 4;
n is an integer of 1 to 4;
p and q are integers of 0 to 3;
X is an oxygen atom (—O—), a sulfur atom (—S—), a carbamyl radical

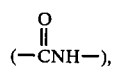

a carbonyl radical

or a carboxy radical

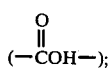

R and R' are ethylene oxide radicals (—O—CH$_2$CH$_2$—);
Q and Z are hydroxy radicals (—OH), carboxy radicals, or alkoxy radicals (—O—alkyl) wherein the alkyl group has 1 to 5 carbon atoms; and
Q and Z can also be substituents described for X linked to form a cyclic compound.

Preferred organic thioether silver halide ripening agents suitable for forming the emulsions of this invention include compounds represented by the formula:

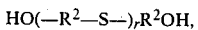

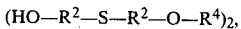

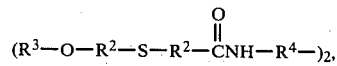

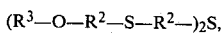

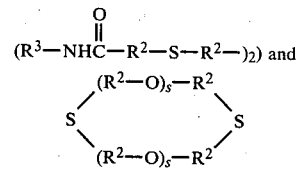

wherein:
r is an integer of 1 to 3;
s is an integer of 1 to 2;
R$^2$ is an alkylene radical having 1 to 5 carbon atoms and is preferably ethylene (—CH$_2$CH$_2$—);
R$_3$ is an alkyl radical having 1 to 5 carbon atoms and is preferably ethyl; and
R$^4$ is an alkylene radical having 1 to 5 carbon atoms and is preferably methylene (—CH$_2$—).

Additional sulfur-containing silver halide ripening agents which are useful in the process of this invention are thiocyanate salts, such as alkali metal, most commonly potassium, and ammonium thiocyanate salts. While any conventional quantity of the thiocyanate salts can be introduced, preferred concentrations are generally from about 0.1 to 20 grams of thiocyanate salt per mole of silver halide in the emulsion being withdrawn from the reaction chamber. Illustrative prior teachings of employing thiocyanate ripening agents are found in Nietz and Russell, U.S. Pat. Nos. 2,222,264, issued Nov. 19, 1940; Lowe et al 2,448,534, issued Sept. 7, 1948; and Illingsworth 3,320,069, issued May 16, 1967, the disclosures of which are incorporated herein by reference.

Any conventional silver halide peptizer can be employed in carrying out the process of this invention. A variety of conventional silver halide peptizers are disclosed, for example, in *Product Licensing Index*, Vol. 92, December 1971, publication 9232, paragraph VIII. Where aqueous silver halide precipitations are contemplated, hydrophilic colloid peptizers are preferred. Gelatin represents a preferred peptizer. Typically gelatin is employed as a peptizer in concentrations from about 0.2 to 10 percent by weight of the silver halide emulsion being produced, most preferably in concentrations from about 0.4 to 5 percent by weight. Exemplary of other preferred polymeric materials which can be used in place of gelatin and gelatin derivatives are materials such as poly(vinyl alcohol), poly(vinylpyrrolidone), polyacrylamides and the copolymers described in U.S. Pat. Nos. 3,692,753 and 3,813,251.

The silver halide emulsions produced according to the process of this invention can form latent images predominantly on the surface of the silver halide grains or predominantely on the interior of the silver halide grains. The properties of the silver halide emulsions can be altered, for example, by introduction of metal dopants in the reaction medium. Typically preferred metal dopants are Group VIII elements having an atomic weight greater than 100, such as ruthenium, rhodium, palladium, osmium, iridium and platinum. The use of metal dopants of this type are disclosed, for example, by Smith and Trivelli U.S. Pat. Nos. 2,448,060, issued Aug. 31, 1948, Berriman 3,367,778, issued Feb. 6, 1968; Wise 3,537,858, issued Nov. 3, 1970; and Evans 3,761,276, issued Sept. 25, 1973.

Silver halide grain morphology can be chosen and controlled by controlling either silver ion or halide ion concentrations within the reaction chamber as discussed, for example, by Gutoff or Terwilliger et al, each cited above, and here incorporated by reference for this teaching. Silver ion and halide ion concentrations at a specific temperature are interrelated. Where a silver salt and a bromide salt, for example, are being introduced concurrently into the reaction chamber at a given temperature, the relationship of the silver and bromide ion concentrations can be expressed by the following equation:

$$-\log KsP = pBr + pAg$$

where
pAg is the negative log silver ion concentration, expressed in normality units,
pBr is the negative log bromide ion concentration, expressed in normality units, and
Ksp is the solubility product constant at the temperature of reaction. The equivalence point is exactly one-half the Ksp for a specific silver halide. The relationship between temperature and $-\log$ Ksp can be seen below in Table I.

TABLE I

| Temperature °C. | AgCl<br>−log Ksp | AgI<br>−log Ksp | AgBr<br>−log Ksp |
|---|---|---|---|
| 40 | 9.2 | 15.2 | 11.6 |
| 50 | 8.9 | 14.6 | 11.2 |
| 60 | 8.6 | 14.1 | 10.8 |
| 70 | 8.3 | — | 10.5 |
| 80 | 8.1 | 13.2 | 10.1 |
| 90 | 7.6 | — | 9.8 |

Techniques for continuously monitoring and regulating pAg during silver halide precipitations are disclosed, for example, by Culhane et al U.S. Pat. No. 3,821,002, issued June 28, 1974, and by Claes and Peelars, Photograpphische Korrespondence, 103, 161 (1967). One common technique for monitoring pAg within a reaction vessel in which silver halide emulsion is being prepared is to monitor the potential difference between an electrode in the reaction chamber and a reference electrode—typically a Ag-AgCl electrode. The potential difference is referred to as vAg and is reported in millivolts. vAg measurements have been empirically correlated to pAg values.

Upon withdrawal of silver halide emulsion from the reaction chamber, further preparation and use can be carried out according to procedures well known in the art in connection with batch prepared silver halide emulsions of similar composition and grain size. The emulsions are, of course, generally useful in forming conventional silver halide photographic elements similarly as comparable batch prepared silver halide emulsions.

In a specifically preferred form the emulsions formed according to the process of this invention are chemically sensitized. Chemical sensitization is most commonly achieved using noble metal and/or middle chalcogen sensitizers. Conventional techniques for achieving noble metal and/or middle chalcogen sensitization are those contained in Sheppard U.S. Pat. Nos. 1,574,944, issued Mar. 2, 1926 and 1,623,499, issued Apr. 5, 1927; Sheppard et al 2,410,689, issued Nov. 5, 1947; Waller et al 2,399,083, issued Apr. 23, 1946; Smith et al 2,448,060, issued Aug. 31, 1948; Baldesiefen 2,540,085 and 2,540,086, both issued Aug. 31, 1948; Damschroder et al 2,597,856, issued May 27, 1952; Damschroder et al 2,642,361, issued June 16, 1953; Dunn 3,297,446, issued Jan. 10, 1967; McVeigh 3,297,447, issued Jan. 10, 1967; McVeigh 3,408,196 and 3,408,197, both issued Oct. 29, 1968; and Millikan et al 3,753,721, issued Aug. 21, 1973. A continuous process for chemical sensitization is described in U.S. Pat. No. 3,827,888, issued Mar. 6, 1972.

As is illustrated by the above patents, a variety of sulfur, selenium and tellurium compounds can be employed as middle chalcogen sensitizers. Typical sulfur sensitizers include compounds such as allyl thiourea, allyl isothiocyanate, phenyl isothiocyanate, phenyl thiourea, carbanilide, thiourea, thiosemicarbazide, sodium, potassium or ammonium thiosulfate, thioacetamide, thioformamide, thiobarbituric acid and diacetylthiourea. Typical selenium sensitizers include compounds such as allyl isoselenocyanate, potassium selenocyanide, allyl selenourea and labile selenium compounds such as colloidal selenium, selenoacetone, selenoacetophenone, tetramethylselenourea, N-($\beta$-carboxyethyl)-N',N'-dimethyl selenourea, selenoacetamide, diethylselenide, triphenylphosphine selenide, tri-p-tolylselenophosphate, tri-n-butylselenophosphate, 2-selenoproponic acid, 3-selenobutyric acid, methyl-3-selenobutyrate, allyl isoselenocyanate and dioctylselenourea. Typical tellurium compounds include allyl isotellurocyanate, potassium tellurocyandide, allyl tellurorea and diacetylthiourea. Other conventional middle chalcogen sensitizers can, of course, be employed. In those instances where an active gelatin is employed in forming the photographic silver halide emulsion no further middle chalcogen sensitization is required.

The noble metal sensitizers typically take the form of salts of gold or Group VIII noble metals, such as ruthenium, rhodium, palladium, iridium, osmium and platinum. Among the noble metal compounds typically employed are compounds such as ammonium and potassium chloropalladate, ammonium, sodium and potassium chloroplatinate, ammonium, potassium and sodium bromoplatinate, ammonium chlororhodate, ammonium chlororuthenate, ammonium chloroiridate, ammonium, potassium and sodium chloroplatinite, ammonium, potassium and sodium chloropalladite, etc. Illustrative gold sensitizers include chloro-potassium aurate, potassium auriaurite, potassium auricyanaide, potassium aurithiocyanate, gold sulfide, gold selenide, gold iodide, potassium chloroaurate, ethylenediamine-bis-gold chloride and various organic gold compounds structurally shown in U.S. Pat. No. 3,753,721, issued Aug. 21, 1973.

While the chemical sensitizers can be added to photographic silver halide emulsions in any conventional manner, it is generally preferred to add the sensitizers concurrently to the emulsions after the silver halide grains thereof have been fully formed. The chemical sensitizers can be added in the form of their aqueous solutions where they are soluble in water or in an innocuous organic solvent where the sensitizer does not have sufficient solubility in water to be used in the form of an aqueous solution. Particularly useful organic solvents include ethanol, methanol, pyridine, acetone, dioxane, etc. That is, organic solvents which have a rather high degree of polarity are usually preferred. Where it is desired to add the sensitizers in some other form than solution, this procedure is also possible, especially where the sensitizers are available in the form of a colloidal suspension. In some cases, it is possible to add the sensitizers suspended in an organic solvent which forms very small suspended particles or oil globules in the photographic emulsion similar to the type of particles produced in preparing coupler dispersions as described in Jelley et al U.S. Pat. Nos. 2,322,027, issued June 15, 1943 and Fierke et al 2,801,171, issued July 30, 1957. Dispersing media useful for this purpose include tricresyl phosphate, dibutyl phthalate, triphenyl phosphate, etc.

The degree to which a photographic silver halide emulsion is sensitized by a middle chalcogen or noble metal sensitizer is a function not only of the quantity of sensitizer added to the emulsion, but also of the time and temperature of digestion following addition of the sensitizer. In sensitizing the emulsions formed in the practice of this invention it is preferred to add concurrently the middle chalcogen and noble metal sensitizers after the silver halide grains of the emulsion are fully formed. In this way it is possible to control the degree of sensitization by each sensitizer by controlling the amount of sensitizer added. The concentration of each sensitizer can be varied depending upon the constrast desired in the final product, the specific sensitizer employed and the photographic speed desired. Typically middle chalcogen sensitizers have been found to be effective in amounts ranging from trace concentrations to 15 mg per mole of silver or more. Preferred concentrations of middle chalcogen sensitizers are typically from 0.1 to 10 mg per mole of silver. Typically noble metal sensitizers are employed in somewhat higher concentrations ranging from about 2 to 5 times that of the middle chalcogen sensitizer. Preferred concentrations of metal sensitizers typically range from about 1 to 40 mg per mole of silver, most preferably from about 1 to 20 mg per mole of silver. It is possible to wash excess sensitizer from the emulsion after digestion of the emulsion.

Other exemplary conventional treatments for the silver halide emulsions can be illustrated by reference to 92 PLI 9232, cited above, pp. 107 through 110. The continuously precipitated emulsions can, for example, be washed to remove soluble salts as described on p. 107, paragraph II, "Emulsion Washing" or by ultrafiltration washing as described in *Research Disclosure* No. 10208 (Oct. 1972). They can be spectrally sensitized with dyes or combinations thereof as described on pp. 108–109, paragraph XV, "Spectral sensitization", of the above article. They can be protected against the production of fog and can be stabilized against loss of sensitivity during keeping by employing the materials described on p. 107, paragraph V, "Antifoggants and stabilizers", of the above article; they can contain development modifiers, hardeners, and coating aids as described on pp. 107–108, paragraph IV, "Development modifiers"; paragraph VII, "Hardeners"; and paragraph XII, "Coating Aids", of the above article; they and other associated layers in photographic elements can contain developing agents, plasticizers, vehicles and filter dyes described on p. 107, paragraph VI, "Developing agents", p. 108, paragraph XI, "Plasticizers and lubricants", and paragraph VIII, "Vehicles", and p. 109, paragraph XVI, "Absorbing and filter dyes", of the above article. They and other layers in photographic elements may contain addenda which are incorporated by using the procedures described on p. 109, paragraph XVII, "Methods of addition", of the above article; and they can be coated using the various techniques described on p. 109, paragraph XVIII, "Coating procedures", on any of the supports described on p. 108, paragraph X, "Supports". Elements containing the above continuously precipitated emulsions can be used in any photographic material sensitive to any kind of electromagnetic radiation to which silver halide is sensitive or can be sensitized to the same extent as comparable batch-prepared emulsions. Among these are color materials, such as those described on p. 110 of the above reference, paragraph XXII, and black-and-white materials which can be either wet- or solution-processed, such as described on p. 110, paragraph XXIII. Suitable emulsions prepared in the above manner can also be used in dry-development, physical development, or direct print processes, as described on pp. 109–110, paragraph XX, "Dry development systems", paragraph XXI, "Physical development systems", and paragraph XXV, "Direct print and print-out". The emulsions can be used for either black-and-white or color image transfer processes such as described on p. 109, paragraph XIX, "Image transfer systems." *Product Licensing Index* and *Research Disclosure* are both publications of Industrial Opportunities Ltd., Homewell, Havant Hampshire, P09, 1EF, United Kingdom.

Several different embodiments of apparatus useful in carrying out the process of this invention are illustrated in the drawings. As shown in FIG. 1, an apparatus adapted to continuous operation of the process of this invention is comprised of a cylindrical hollow chamber 1 equipped with a rotatable agitator 2 provided with flexible blades 3, made of a suitable material such as rubber. Hollow chamber 1 is partially filled with spherical beads 5 of a suitable size and composition, such as glass beads with a diameter of 2 millimeters. Inlet tubes 6 and 7 communicate with the interior of hollow chamber 1 to permit introduction of two different solutions into the bed of beads 5 which is supported on grid 4. Hollow chamber 1 is connected at its lower end to downwardly slanting outlet tube 11 which is equipped at its lower end with an exit nozzle 8 provided with a plunger 9 connected to a float 10. Grid 4 supports the beads 5 while permitting the crystalline precipitate formed in chamber 1 to pass through tube 11 and out exit nozzle 8. Float 10 is adapted to assure a substantially constant level of liquid in chamber 1 at the liquid level indicated by the line N-N. The apparatus illustrated is especially adapted to the preparation of crystalline powders that are sufficiently dense that they sink to the bottom of the crystallization chamber for recovery through outlet tube 11.

Figure 2:
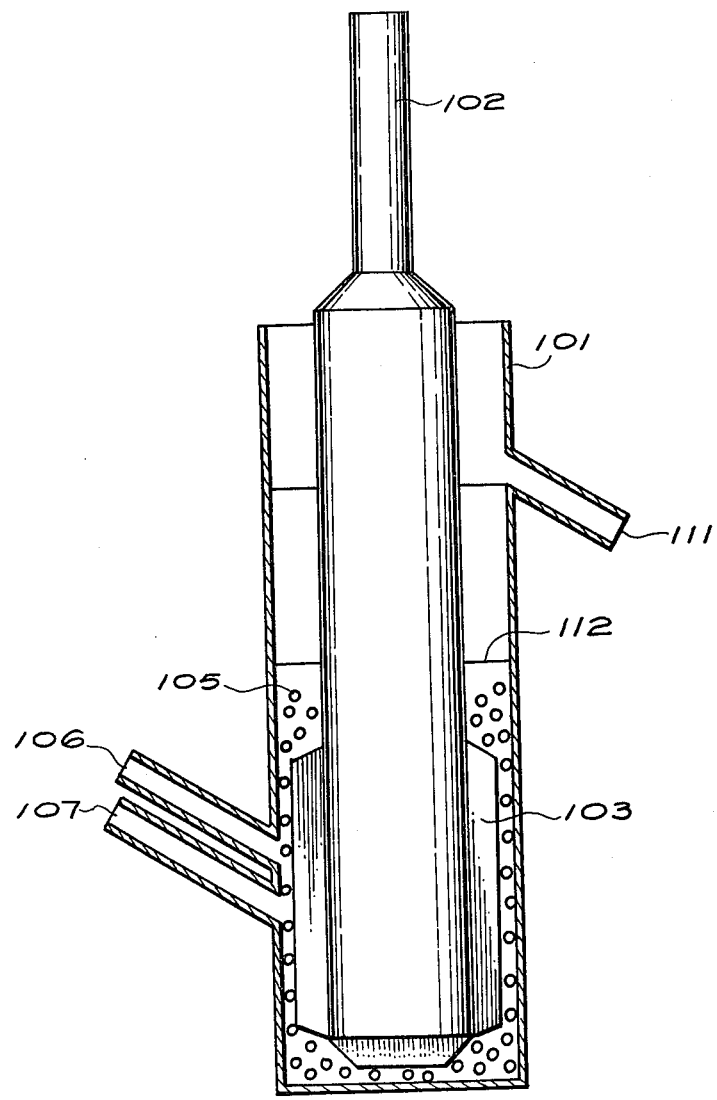
FIG. 2 is a sectional view of one embodiment of apparatus adapted to continuous preparation of low-density crystalline powders by the method of this invention.

FIG. 2 illustrates an apparatus that is adapted to the continuous operation of the process of this invention with low density crystalline powders that are most easily recovered at the top of the crystallization chamber. The apparatus is comprises of a hollow cylindrical chamber 101 equipped with a rotatable agitator 102 provided with flexible blades 103. Hollow chamber 101 is partially filled with spherical beads 105 and is equipped with inlet tubes 106 and 107 which communicate with the interior of hollow chamber 101 to permit introduction of two different solutions into the bed of beads 105. A foraminous ring 112 fits within chamber 101 to confine beads 105 to the lower portion of chamber 101 and to prevent the formation of vortices. Evacuation of the crystalline precipitate is carried out through outlet tube 111 which is arranged to slant downwardly and is in communication with the interior of the upper portion of chamber 101.

While the apparatus illustrated in FIGS. 1 and 2 is very effective for carrying out the method of this invention, various changes can be made in the design of the apparatus to suit particular circumstances, as desired. For example, the hollow cylindrical chambers can be of a double wall construction so that a liquid which is maintained at a constant temperature can be circulated within the space between the walls. As a further example, the inlet tubes can be diametrically opposite rather than being situated one above the other as shown.

Figure 3:
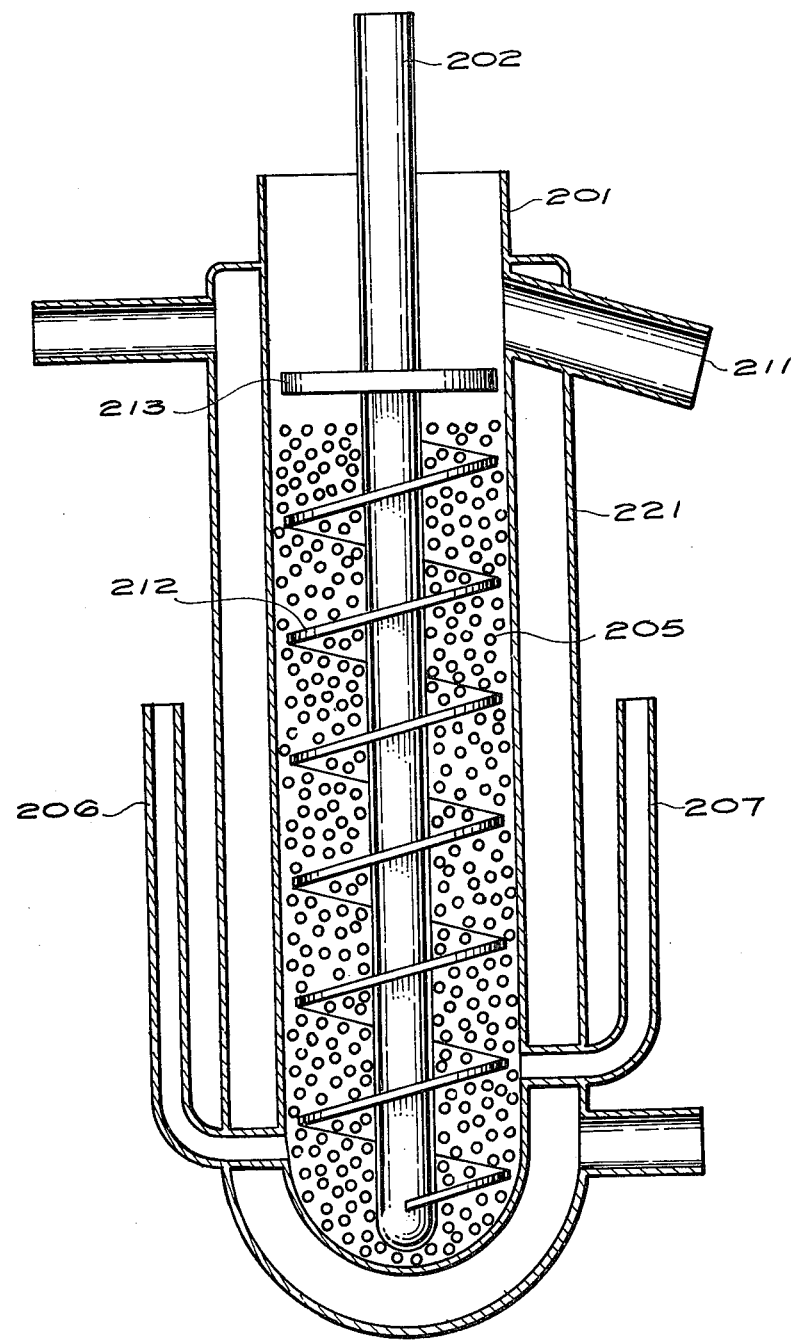
FIG. 3 is a sectional view of an alternative embodiment of apparatus adapted to continuous preparation of low-density crystalline powders by the method of this invention.

FIG. 3 illustrates an alternative embodiment of apparatus designed for the continuous preparation of low density crystalline powders. The apparatus is comprised of a hollow cylindrical chamber 201, provided with a sleeve 21 for circulation of a fluid maintained at a desired temperature and equipped with a rotatable agitator 202 having a plurality of sloping disks 212 attached thereto. A ring 213 secured to the shaft of agitator 202 restrains beads 205 within chamber 201. The apparatus is provided with inlet tubes 206 and 207 for introduction of liquids into the bed of beads 205 and with outlet tube 211 for evacuation of the crystalline precipitate.

Figure 4:
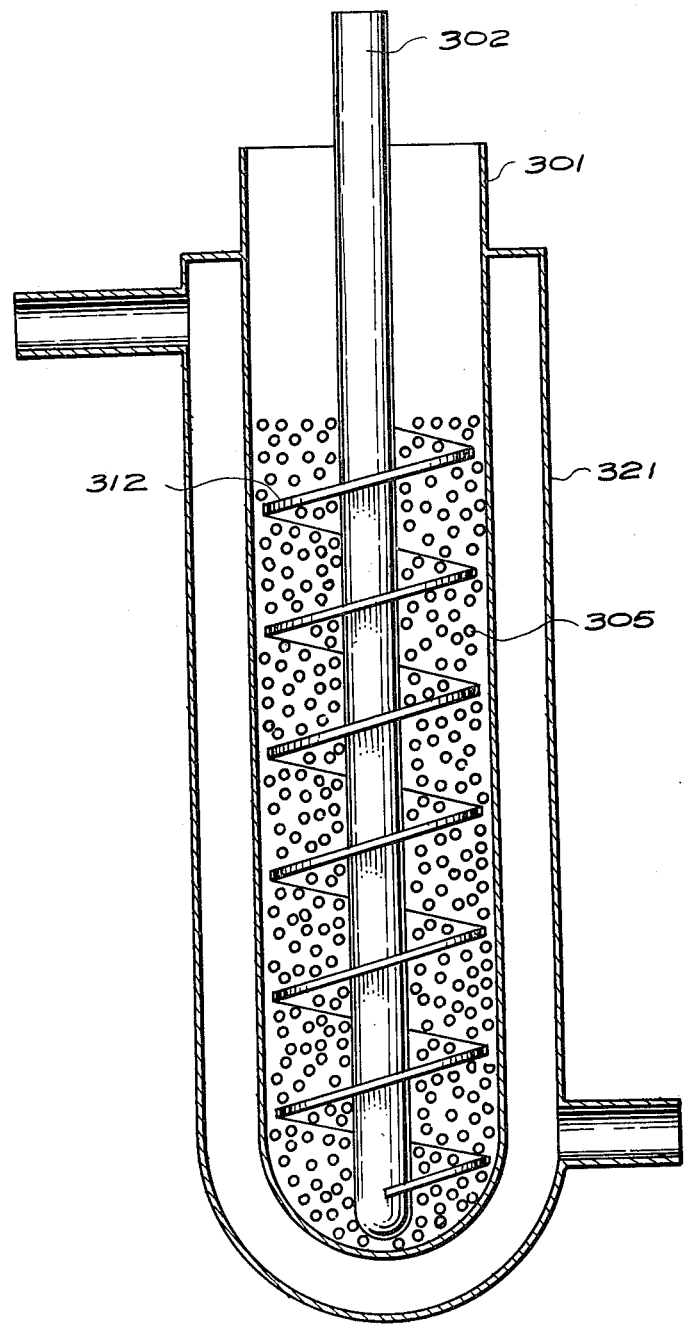
FIG. 4 is a sectional view of an apparatus adapted to intermittent preparation of crystalline powders by the method of this invention.
Figure 5A:
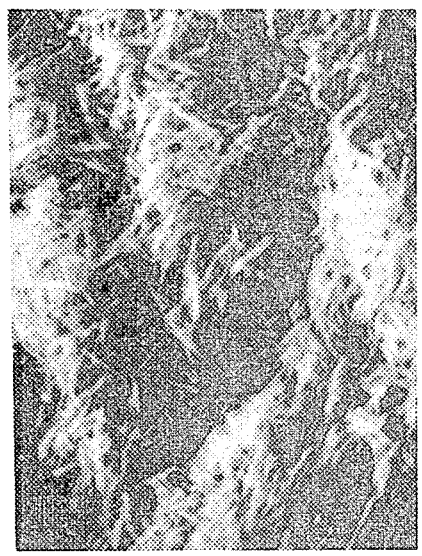
FIG. 5 is a series of photomicrographs comparing crystals made by the method of this invention with crystals made by procedures outside the scope of the invention.
Figure 5B:
Figure 5C:
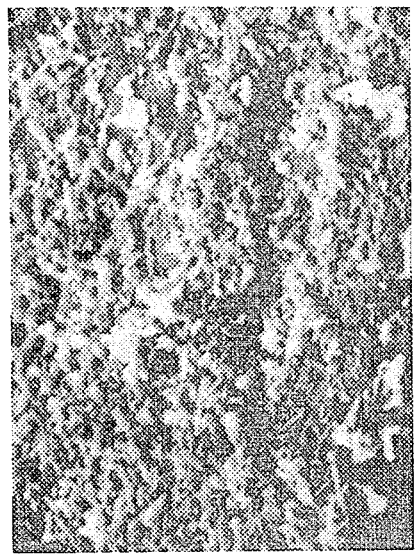
Figure 5D:
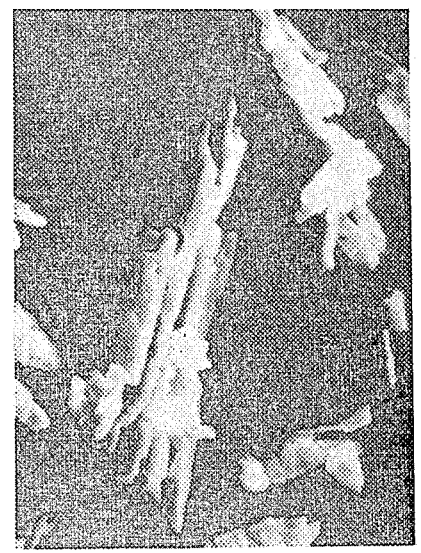
Figure 5E:
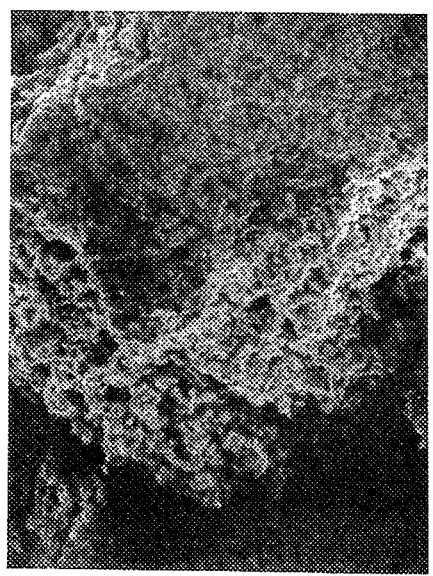
Figure 5F:
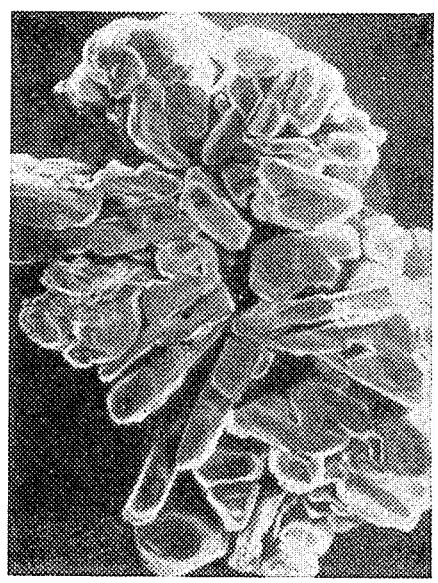

FIG. 4 illustrates an alternative embodiment of the apparatus that is adapted for intermittent operation of the process. The apparatus is comprised of a hollow cylindrical chamber 301, partially filled with beads 305, provided with a sleeve 321 for circulation of a fluid maintained at a desired temperature and equipped with a rotatable agitator 302 having a plurality of sloping disks 312 attached thereto.

The invention is further illustrated by the following examples of its practice.

EXAMPLE 1

This example illustrates the use of the method of this invention in a reaction-crystallization process in which iron/cobalt oxalate crystals are formed by reaction of oxalic acid with iron chloride and cobalt chloride.

An apparatus similar to that illustrated in FIG. 3, having a cylindrical glass chamber 201 which is 4 centimeters in diameter and 26 centimeters in height was partially filled with glass beads 205 having a diameter of 5 millimeters. The temperature inside chamber 201 was maintained at 10° C. by circulation of water in sleeve 221. A solution "A" was prepared by dissolving 1500 grams of oxalic acid ($H_2C_2O_4.2H_2O$) in 20 liters of distilled water and a solution "B" was prepared by dissolving 1080 grams of ferrous chloride ($FeCl_2.4H_2O$) and 1300 grams of cobalt chloride ($CoCl_2.6H_2O$) in 6 liters of distilled water. A sufficient quantity of solution "A" was introduced into chamber 201 to cover the bed of glass beads 205 and stirrer 202 was started and maintained at a speed of 800 revolutions per minute. Using a volumetric pump, solution "A" was continuously pumped into chamber 201 through inlet tube 206 at a flow rate of 70 milliliters per minute. Using a second volumetric pump, solution "B" was continuously pumped into chamber 201 at a flow rate of 21 milliliters per minute. The region wherein solutions "A" and "B" intermix became colored and a yellow precipitate was immediately formed. After allowing several minutes for the system to reach a steady state of operation, a sample of the crystals evacuated through outlet tube 211 was taken and identified as sample "a". A second sample, identified as sample "a'", was taken one hour later.

For purposes of comparison, a second apparatus identical to that described above except that the glass beads were omitted was used to prepare the crystalline precipitate. Solution "A" was continuously pumped to the apparatus at a flow rate of 70 milliliters per minute and solution "B" was continuously pumped to the apparatus at a flow rate of 21 milliliters per minute while agitor 202 was rotated at a speed of 800 revolutions per minute. After an incubation period of several seconds, a crystalline precipitate was formed. A sample of this precipitate was taken and identified as sample "b".

Each of samples "a", "a'" and "b" was examined with an electron scanning microscope. It was found that samples "a" and "a'" were identical, thereby establishing that the characteristics of the product produced by the process of this invention do not change once the process is operating at steady state conditions. The microscopic examination showed that samples "a" and "a'" were acicular crystals having a narrow size distribution and a size of approximately one micron and that the crystals were morphologically homogeneous. In contrast, the microscopic examination showed that the crystals of sample "b" were larger than those of samples "a" and "a'", and were heterogeneous in morphology and characterized by a broad size distribution. The photomicrographs of samples "a" and "b" are shown in FIG. 5, in parts a and b respectively, at a magnification of 8000 times.

EXAMPLE 2

This example illustrates the use of the method of this invention in a reaction-crystallization process in which silver bromide crystals are formed by reaction of potassium bromide and silver nitrate.

An apparatus similar to that illustrated in FIG. 1 having a cylindrical glass chamber 1, which is 4 centimeters in diameter and 10 centimeters in height, was partially filled with glass beads 5 having a diameter of 2 millimeters. Chamber 1 was filled to level NN with a one molar solution of potassium nitrate at 40° C. and agitator 2 was started and operated at a speed of 1000 revolutions per minute. By means of volumetric pumps, a one molar solution of potassium bromide containing 3% of acylated gelatin was introduced through inlet tube 6 at a flow rate of 5 milliliters per minute and a one molar solution of silver nitrate was introduced through inlet tube 7 at a flow rate of 5 milliliters per minute. The potassium bromide and silver nitrate solutions were each at a temperature of 40° C. and chamber 1 was insulated against heat loss so that a temperature of 40° C. was maintained during the reaction.

After several minutes of operation, the vAg stabilized at around 200 mV (the vAg being the potential measured between an electrode with a silver bromide surface, positioned in the lower portion of the reactor underneath grid 4, and a Ag-AgCl reference electrode.) Normal steady state operation of the system is, accordingly, attained within several minutes. A sample of the silver bromide crystals recovered through exit nozzle 8 was taken at the end of 10 minutes of operation and a second sample was taken after one hour of operation. Each of the samples was examined with an electron scanning microscope and found to be identical, indicating that the characteristics of the product are constant when the process is operating under steady state conditions. The silver bromide emulsions obtained in this process were found to be characterized by morphological homogeneity and reduced heterodispersity (and therefore higher contrast) as compared to silver bromide emulsions produced by back-mixed continuous silver halide precipitation processes.

EXAMPLE 3

This example illustrates the preparation of photographic silver chloride emulsions.

An apparatus essentially simlilar to that of FIG. 1 and Example 2 was employed, except that the inlets for the silver salt and the halide salt were located at the same horizontal level on diametrically opposite sides of the reactor. The reaction chamber was filled with polyethylene beads of 3 millimeter diameters. Filled with beads the liquid volume of the reactor to the lower edge of the inlets was 68 ml.

The following solutions were prepared:

| Solution A | |
|---|---|
| Bone Gelatin | 400 g |
| Water to | 10.0 liters |
| Solution B | |
| NaCl | 234 g |
| Water to | 4 liters |
| Solution C | |
| AgNo$_3$ | 680 g |
| Water to | 4 liters |

Distilled water was employed in each instance and the temperature of the solutions was maintained at 85° C.

Solution A, the peptizer, was added to the apparatus from the top through the annular opening between the chamber element and the spindle at a rate of 102 ml/min. The spindle was rotated at 300 rpm. Solutions B and C were added simultaneously and separately through the inlets at a rate of 51 ml/min. These rates of addition gave a residence time within the reactor of 20 seconds. The temperature of the contents of the reaction chamber averaged 68° C.

In several successive runs the vAg within the reaction chamber under steady state operating conditions was monitored and maintained at 180 millivolts, 160 millivolts, 140 millivolts, 120 millivolts, 100 millivolts and 80 millivolts by adjustment of the vAg of Solution A by addition of a small amount of Solution B thereto and by the regulation of the feed rates of Solutions B and C. In each instance the emulsions were less heterodispersed than comparable emulsions manufactured by the usual continuous processes. The silver chloride grains produced at the highest vAg were of the smallest average grain size and of cubic morphology. As the vAg decreased, the silver chloride grains became larger and more rounded.

EXAMPLE 4

This example illustrates the utility of longer residence times. Except as indicated below, silver chloride emulsion preparations are identical to those of Example 3.

The following solutions were employed:

| Solution A | |
|---|---|
| Bone Gelatin | 160 g |
| Water to | 4.0 liters |
| Solution B | |
| NaCl | 59 g |
| Water to | 1 liter |
| Solution C | |
| AgNo$_3$ | 170 g |
| Water to | 1 liter |

The rate of introduction of the peptizer was reduced to 2.6 ml/min, and the rate of introduction of each of silver and halide salt solutions was reduced to 1.3 ml/min. This resulted in a residence time of 5 minutes being obtained. The temperature of the contents of the reaction chamber averaged 36° C. In performing silver chloride emulsion preparations at different vAg levels generally similar results were obtained as in Example 3, except that the sizes of the silver chloride grains were much larger. The size increase was, of course, expected because the longer residence time affords an extended period for silver halide crystal growth to occur. At 180 mv vAg in Examples 3 and 4 the silver chloride grains were of comparable morphological character—that is, they were cubic and showed no rounding. Examples 3 and 4 considered together illustrate that in order to obtain silver chloride grains of large grain size it is not necessary to alter the vAg parameter, since the larger grain sizes can be achieved by increasing residence time. Further, with longer residence times being employed to increase grain size no alteration in morphological character occurs, whereas this is not the case in varying vAg.

Example 4 was repeated, except that the beads were omitted from the reaction chamber and the flow rates were adjusted to hold the residence time constant at 5 minutes. The results were qualitatively identical to those of Example 4, except that it was noted that larger silver chloride crystals were produced in the absence of the beads.

EXAMPLE 5

This example illustrates the use of the method of this invention in a purification-crystallization process in which glycine is purified by precipitating it from aqueous solution through the addition of ethyl alcohol.

An apparatus similar to that illustrated in FIG. 2, having a stainless steel chamber 101, 4 centimeters in internal diameter and 20 centimeters in height, was partially filled with stainless steel beads 105 having a diameter of 2 millimeters. Ethyl alcohol was added to chamber 101 to a height covering the bed of beads 105 and agitator 102 was rotated at a speed of 1000 revolutions per minute. A solution of 100 grams of glycine (an amino acid having the formula $NH_2CH_2COOH$) dissolved in 500 milliliters of distilled water was introduced into chamber 101 at a flow rate of 20 milliliters per minute through inlet tube 107 and ethyl alcohol was introduced into chamber 101 at a flow rate of 60 milliliters per minute through inlet tube 106. A crystalline precipitate was immediately formed and evacuated through outlet tube 111. A sample of the crystalline precipitate was taken and identified as sample "c".

For purposes of comparison, 50 milliliters of the glycine solution described above was poured into a beaker containing 15 milliliters of ethyl alcohol and the solution was agitated with a conventional impeller-type stirrer. A sample of the crystalline precipitate which formed was taken and identified as sample "d⇌.

Each of samples "c" and "d" was examined with an electron scanning microscope and it was found that the crystals of sample "c", as compared to those of sample "d", were of smaller size and possessed a narrower size distribution and greater morphological homogeneity. The photomicrographs of samples "c" and "d" are shown in FIG. 5, parts c and d respectively, at a magnification of 600 times.

EXAMPLE 6

This example illustrates the use of the method of this invention in a purification-crystallization process in which orthoboric acid is purified by precipitating it from aqueous solution as a result of reduction in the temperature of the solution.

An apparatus similar to that illustrated in FIG. 4, having a cylindrical copper chamber 301, was partially filled with particles of granulated copper having a size approximately 2 millimeters in diameter. A solution was prepared by dissolving 200 grams of orthoboric acid in one liter of distilled water and heating to close to the boiling point and this solution was introduced into chamber 301 while agitator 302 was rotated at a speed of 600 revolutions per minute and hot water at a temperature of 90° C. was circulated within sleeve 321. In order to cool the solution in chamber 301, the flow of hot water to sleeve 321 was stopped and replaced with a flow of cold water at 20° C. Within several minutes the temperature of the solution was reduced to room temperature and a white precipitate formed. The precipitate was separated from the granulated copper and a sample was taken and identified as sample "e".

For purposes of comparison a second apparatus identical to that discussed above except that the granulated copper was omitted was used to precipitate the orthoboric acid under identical conditions. A sample of the precipitate formed in this manner was taken and identified as sample "f".

Each of samples "e" and "f" was examined with an electron scanning microscope and it was found that the crystals of sample "e", as compared to those of sample "f", were of smaller size and possessed a narrower size distribution and greater morphological homogeneity. The photomicrographs of samples "e" and "f" are shown in FIG. 5, parts e and f respectively, at a magnification of 200 times.

The invention has been described in detail with particular reference to preferred embodiments thereof, but it will be understood that variations and modifications can be effected within the spirit and scope of the invention.

We claim:

1. In a process of continuously preparing a radiation-sensitive silver halide emulsion wherein
   an aqueous silver salt solution and an aqueous halide salt solution capable of reacting to form radiation-sensitive silver halide grains are concurrently and separately introduced through inlets to a reaction chamber in the presence of a peptizer and
   radiation-sensitive silver halide emulsion is withdrawn at an outlet from the reaction chamber while silver halide grain formation is occurring under steady state operating conditions
   the improvement comprising
      reacting the silver salt and the halide salt within the reaction chamber in the presence of the peptizer in a bed of small, inert, continuously moving solid particles.

2. In a process according to claim 1 the further improvement wherein the particles are glass or organic polymer beads.

3. In a process according to claim 1 the further improvement wherein the particles are spherical and have a diameter in the range of from about 0.1 to about 10 millimeters.

4. In a process according to claim 3 the further improvement wherein the particles have a diameter in the range of from about 0.1 to 3 millimeters.

5. In a process according to claim 1 the further improvement wherein the inlets are located above the outlet and the direction of the liquid flow is downward.

6. In a process according to claim 1 the further improvement wherein the silver halide is a silver bromide.

7. In a process according to claim 1 the further improvement wherein the silver halide is silver chloride.

8. In a process according to claim 1 the further improvement wherein the peptizer is gelatin.

9. In a process according to claim 1 the further improvement wherein the residence time within the reaction chamber is in the range of from about 10 seconds to about 10 minutes.

10. In a process according to claim 9 the further improvement wherein the residence time within the reaction chamber is in the range of from about 20 seconds to about 5 minutes.

11. A process as claimed in claim 1 wherein the silver halide grains are formed in the presence of a sulfur-containing ripening agent.

* * * * *